United States Patent [19]
Arnett et al.

[11] Patent Number: 5,460,604
[45] Date of Patent: Oct. 24, 1995

[54] SURGICAL IRRIGATION APPARATUS

[75] Inventors: Jeffrey D. Arnett, Kalamazoo; David H. Grulke, Battle Creek, both of Mich.

[73] Assignee: Stryker Corporation, Kalamazoo, Mich.

[21] Appl. No.: 158,512

[22] Filed: Nov. 29, 1993

[51] Int. Cl.⁶ .......................... A61M 7/00; A61B 17/32
[52] U.S. Cl. .................. 604/35; 606/131; 604/40
[58] Field of Search .................. 604/27, 28, 30, 604/35, 39, 43, 275, 289, 310, 902; 606/131; 239/488, 501, 504, 520, 552; 15/320, 321, 322

[56] References Cited

U.S. PATENT DOCUMENTS

| | | | |
|---|---|---|---|
| 487,655 | 12/1892 | Wardell | 604/39 |
| 609,280 | 8/1898 | King | 604/275 |
| 611,454 | 9/1898 | Longden | 604/275 |
| 1,017,638 | 2/1912 | McCoole | 239/552 |
| 1,758,119 | 5/1930 | LeMoon | 239/552 |
| 3,640,472 | 2/1972 | Hruby, Jr. et al. | 239/552 |
| 3,713,423 | 1/1973 | Sparr, Sr. | 604/289 |
| 3,797,755 | 3/1974 | Saisho | 239/552 |
| 4,692,140 | 9/1987 | Olson | 604/35 |
| 4,904,238 | 2/1990 | Williams | 604/35 |
| 5,037,431 | 8/1991 | Summers et al. | 606/131 |
| 5,046,486 | 9/1991 | Grulke et al. | 128/66 |
| 5,269,750 | 12/1993 | Grulke et al. | 604/21 |

FOREIGN PATENT DOCUMENTS 1377120  2/1988  U.S.S.R. .................. 604/28

OTHER PUBLICATIONS

Copy of Stryker Brochure No. 4500 001 121 JJB, dated Dec. 1988 which in the lower left photo shows several alternative EXCEL (TM) tips (including the 207–110 Excel Multi Orifice Tip) (1 page).

Copy of p. 24 of Davol/Bard Brochure, which drawings identify several of their tips, including Model Nos. 3760, 3773, 3771, etc. (1 page) (no date).

Copy of Zimmer Brochure—PULSAVAC Wound Debridement System and assorted irrigation outlet tips, including Model 5150-81 and Model 5150-85 (1 page) (no date).

*Primary Examiner*—Stephen C. Pellegrino
*Assistant Examiner*—Nancy Mulcare
*Attorney, Agent, or Firm*—Flynn, Thiel, Boutell & Tanis

[57] ABSTRACT

A tip member is to be fixed adjacent the distal end of the irrigation outlet tube of a surgical irrigation handpiece. The tip member modifies the irrigation liquid flow to direct same forwardly toward a surgical site as a hollow, divergent, substantially circumferentially continuous, generally funnel-shaped wash of irrigation liquid and thereby for wetting substantially the perimeter of a circle, rather than the center of such circle, on the surgical site, at a given instant.

17 Claims, 3 Drawing Sheets

FIG. 8

SURGICAL IRRIGATION APPARATUS

This invention relates to surgical irrigation apparatus and particularly to a wand for a surgical suction-irrigation handpiece.

BACKGROUND OF THE INVENTION

Grulke et al U.S. Pat. No. 5,046,486, assigned to the assignee of the present invention, discloses a suction-irrigation handpiece including a forward extending, elongate wand comprising irrigation and suction tubes, through which, respectively, a pulsed irrigation liquid is applied to a surgical site and flowable materials are suctioned from the surgical site. This device has been marketed by the present assignee, Stryker Corporation, of Kalamazoo, Mich., under the trademark EXCEL.

The EXCEL (TM) device has been sold with a straight cylindrical irrigation outlet flow port. In addition, the EXCEL (TM) device has been sold with a modified tip member in which the irrigation outlet flow path is blocked by a coaxially close spaced pair of radially extending disks each having four, evenly circumferentially spaced, axial through holes. The forward disk is angularly offset through 45°, about the common axis of the two disks, with respect to the rearward disk, so that irrigation flow through the holes in the first disk hits the forward disk between the holes therein, filling the space between the disks with a circumferentially turbulent mass of irrigation liquid, from which liquid eventually escapes through the circumferentially offset holes in the forward disk. The result is a substantially solid cross-sectional flow of conical profile, forward from the forward disk or, in other words, a substantially solid, forwardly travelling, radially diverging, solid stream. With such tip member used with the EXCEL (TM) handpiece, such stream is axially broken into a series of axially substantially discrete, generally disk-like slugs, or pulses. While this tip member tends to reduce the force of impact of each liquid pulse on the surgical site, and spread same over a larger area, it also, undesirably, substantially reduces the irrigation liquid flow rate to the surgical site (substantially reduces the irrigation liquid delivered per unit time at the surgical site).

The present assignee also markets an improved pulsed irrigation-suction handpiece, capable of more forceful, sharply defined, irrigation liquid pulses, under the trademark SURGILAV PLUS.

In both of the above-mentioned suction-irrigation handpieces, the suction and irrigation tubes are coaxially telescoped and form a removable wand which extends forward from the housing of the handpiece. The irrigation liquid tube is of lesser diameter than, and is coaxially disposed within the larger diameter suction tube. The tubes are radially fixed one within the other, with an annular suction passage radially between the two, by structure at the proximal and distal ends of the tubes. The structure at the distal ends of the tubes comprises circumferentially spaced, radially extending fins extending radially outward from the distal end of the irrigation tube to engage the interior surface of the suction tube. The handpiece is actuable by a surgeon, or surgical assistant, to forcibly forwardly expel pulses of irrigation liquid from the distal end of the irrigation tube and to suction a flowable material from the surgical site, into the distal end of the suction tube and thus into the annular space surrounding the irrigation tube.

The SURGILAV PLUS (TM) device is capable of unusually forceful, sharply defined irrigation liquid pulses and is thus particularly effective for difficult surgical site cleaning jobs wherein unwanted bits of tissue or the like may be difficult to remove from surfaces at the surgical site. For example, the SURGILAV PLUS (TM) device has been found particularly effective in cleaning bits of soft tissue out of a femoral cavity in preparation for cementing therein of the elongate, ball-supporting stem of a hip joint prothesis.

However, the present Applicant has noted that use of the same suction irrigation handpiece for medical/surgical procedures with substantially different requirements (for example in terms of force and pattern of irrigation liquid output from the handpiece), would help limit increase of medical costs to the public, for example by limiting the number of different types of suction-irrigation handpieces needed to be designed, manufactured and inventoried by suppliers and bought and inventoried by medical practitioners.

Applicant has further noted that it is in some instances desirable to use a relatively gentle irrigation of tissue, wherein application of irrigation liquid pulses to tissue at the full force capability of the SURGILAV PLUS (TM) handpiece, for example, would risk damage of tissue. An example is the cleaning of tissue in trauma cases, such as a skin abrasion resulting from skidding road contact with the skin in a fall from a moving motorcycle, wherein foreign particles (dirt, sand, and other particulate material) contaminating the skin abrasion area need to be removed prior to further medical treatment. However, Applicant notes that it is desirable to avoid reduction in flow rate (unit volume per unit time) of irrigation liquid to the trauma site.

Accordingly, the objects and purposes of the present invention include provision of a tip member for a surgical irrigation wand for varying the nature of irrigation flow from an irrigation handpiece, particularly to adapt to wider area cleaning of more delicate and easily injured tissue, including use in helping to clean trauma sites.

SUMMARY OF THE INVENTION

A tip member is to be fixed adjacent the distal end of the irrigation outlet tube of a surgical irrigation handpiece. The tip member modifies the irrigation liquid flow to direct same forwardly toward a surgical site as a hollow, divergent, substantially circumferentially continuous, generally funnel-shaped wash of irrigation liquid and thereby for wetting substantially the perimeter of a circle, rather than the center of such circle, on the surgical site, at a given instant.

Other objects and purposes of the invention will be apparent to persons acquainted with apparatus of this type upon reading the following description and inspecting the accompanying drawings.

DETAILED DESCRIPTION

The present invention may be practiced in connection with a handpiece 10. The handpiece 10 schematically shown in FIG. 1 may, for example, be of a kind marketed by Stryker Corporation under the trademark SURGILAV PLUS (TM), and disclosed in copending application Ser. No. 08/049,144 (attorney reference Stryker Case 130), assigned to the assignee of the present invention. Such a handpiece 10 includes a substantially pistol-shaped housing 11 comprising a forward extending barrel 12 and a hand-engageable handle 13 depending from the rear portion of the barrel 12. A motor M, for example an electric motor M, fixedly mounted in the handle 13 drives, by any convenient means schematically indicated in FIG. 1, a pump P for irrigation liquid, which pump is located in the barrel 12.

Figures 1, 2, 3:
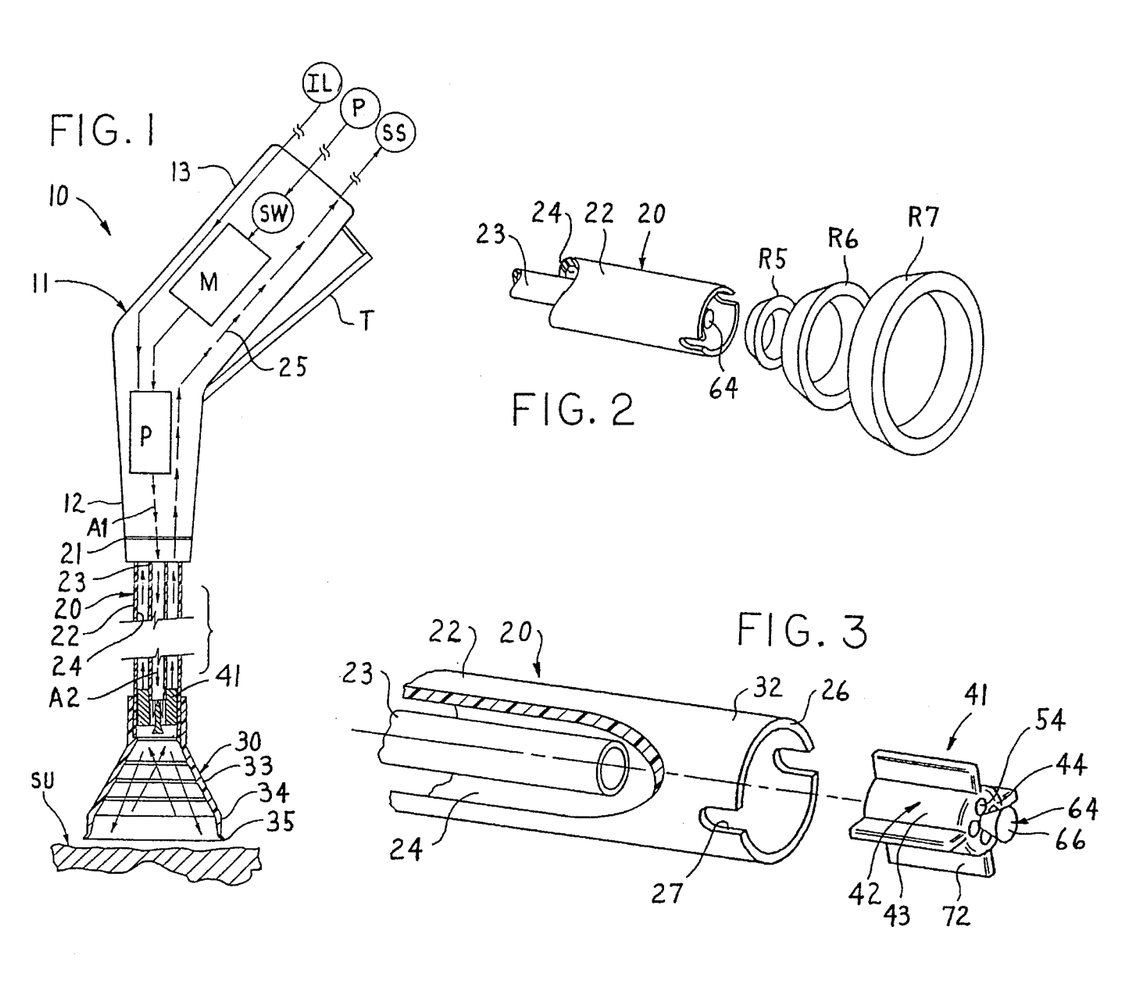
FIG. 1 is a schematic view of a suction irrigation handpiece having a forwardly extending, preferably removable and replaceable, suction-irrigation wand including a tip member embodying the invention, the showing of the wand being fragmentary.
FIG. 2 is an enlarged fragmentary pictorial view of the distal (forward) end of the FIG. 1 wand, including a schematic representation of the irrigation liquid outflow pattern from the FIG. 1 tip member.
FIG. 3 is an enlarged, fragmentary, partially broken, exploded view of the FIG. 2 structure.

An elongate flow directing wand 20 extends forward from the barrel 12 and preferably is releasably fixable thereto, as schematically indicated at 21.

The wand 20 comprises an outer suction tube 22 loosely and coaxially surrounding an inner irrigation tube 23 and thereby defining an annular suction passage 24 radially therebetween. As schematically indicated in FIG. 1, the motor M is energizable through a switch SW from a suitable power source, for example an electric power source EP, by manual actuation of a trigger T to actuate switch SW. The pump P is supplied with irrigation liquid from an irrigation liquid source IL and supplies irrigation liquid pulses to the irrigation tube 23 in response to actuation of the motor M.

The suction tube 22 connects through a suitable passage, schematically indicated by the arrows 25 in FIG. 1, with a suction source SS in a conventional manner. The handpiece 10 may or may not be equipped with a manual control for turning on and off suction to the suction tube 22, as in the EXCEL (TM) device or SURGILAV PLUS (TM) device, respectively, above described.

The distal end 26 of the suction tube 22 may for example be provided with front opening notches 27 (FIG. 3) to facilitate passage of flowable materials from a surgical site SU into the suction tube 22 if the distal end 26 of the suction tube 22 is brought close to the surface of the surgical site.

While the present invention was developed with handpieces of the type as schematically disclosed with FIG. 1 in mind, it will be understood that the present invention is useable with medical irrigation apparatus of other kinds, for example non-suction handpieces, steady stream rather than pulsed irrigation output sources, different means to pressurize the irrigation liquid, and so forth.

In the unit shown in FIG. 1, a funnel-shaped spray shield 30 extends divergently forward from the distal end 26 of the suction tube 22. As shown in more detail in FIG. 6, the funnel-shaped spray shield 30 has a cylindrical proximal neck 31 frictionally sleeved over the distal end portion 32 of the suction tube 22. The neck 31 of the spray shield can easily be slid on to and off of the distal end portion 32 of the suction tube 22 as desired, such that the suction tube 22 can be used with or without the spray shield as the surgeon prefers. The spray shield 30 has a frustoconical bell 33 (FIG. 1) which extends divergently forwardly from the suction tube 22. A forward rim 34 at the front end of the bell 33 here terminates an axially short, forward flaring and feathering lip 35. The lip 35 can be brought close to (as in FIG. 1), or into actual contact with, the surface of the surgical site SU, to reduce or eliminate sideward splashing of irrigation liquid as it hits the surface of the surgical site SU and thereby protect surgical personnel from splashing liquid.

The proximal (rear) end portion of the irrigation tube 23 is fixed, by means not shown, preferably coaxially, in the area of the releasable connection 21, with respect to the suction tube 22. The front (distal) end of the irrigation tube 23 is fixed, preferably coaxially, with respect to the distal end portion 32 of the suction tube 22.

To the extent above described, the apparatus is available on the market, for example as the abovementioned apparatus sold under the trademark SURGILAV PLUS by Stryker Corporation of Kalamazoo, Mich., the present assignee.

Turning now to aspects of the disclosed apparatus more closely related to the present invention, the distal end portion 40 (FIG. 6) of the irrigation tube 23 terminates behind the distal end 26 of the suction tube 22 and is located coaxially within the suction tube 22 by support of a tip member 41 (FIGS. 3–7). The tip unit 41 is preferably a rigid, one-piece member of molded plastics material, for example, a modified acrylic, such as CYROLITE (TM) available from Cyro Industries located at Mt. Arlington, N.J.

The tip member comprises an elongate body 42 having a preferably circular, cylindrical, outer perimeter surface 43 (FIG. 3) terminating forwardly in a distal end wall 44 having a substantially planar distal end face preferably perpendicular to the central axis of the tip member and the tubes 22 and 23 with which it is associated. The tip member 41 further comprises a proximal end 45 (FIGS. 5–7) having a central, coaxial, proximally opening and preferably cylindrical recess 46 for snugly but slideably receiving the distal end portion 40 (FIG. 4) of the irrigation tube 23 therein. Thus, in the manner shown in FIG. 4, the tip member 41 is rearwardly sleeveable over the front end of the irrigation tube. The tip member 41 is thus cantilevered forwardly from the irrigation tube in coaxial alignment therewith. The tip member 41 may be fixed on the front end of the irrigation tube 23 by any convenient means, such as adhesive bonding. When thus installed, the distal end 50 of the irrigation tube 23 abuts, or comes close to abutting, the rear facing end wall 51 of the recess 46.

A central, coaxial, conical core 52 (FIGS. 5–7) is integral with and tapers rearwardly (leftwardly in FIG. 6) from the distal end wall 44 for forwardly diverging the flow of irrigation liquid therealong. The conical core 52 is thus rearwardly fixedly cantilevered from the distal end wall 44. The conical core 52 is coaxial with the recess 46 and its pointed rear end 53 is substantially coplanar with the end wall 51 (FIG. 7) of the recess 46.

A cylindrical, reduced diameter, coaxial, circular cross-section, forward extension 46E of the recess 46 has a perimeter wall 47E (FIG. 7) extending forward from the end wall 51 of recess 46. The extension recess perimeter wall 47E extends forward to the distal end wall 44 of the body 42. The conical core 52 diverges forwardly until it meets the perimeter wall 47E of the recess extension, at the distal end wall 44 of the tip member body 42, as seen in FIG. 7.

Figure 5:
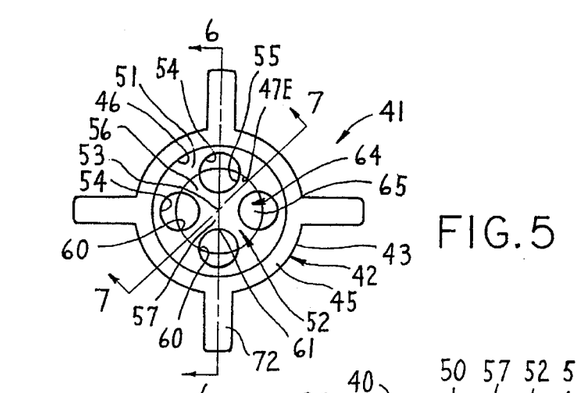
FIG. 5 is an enlarged rear view of the FIG. 3 tip member.
Figure 6:
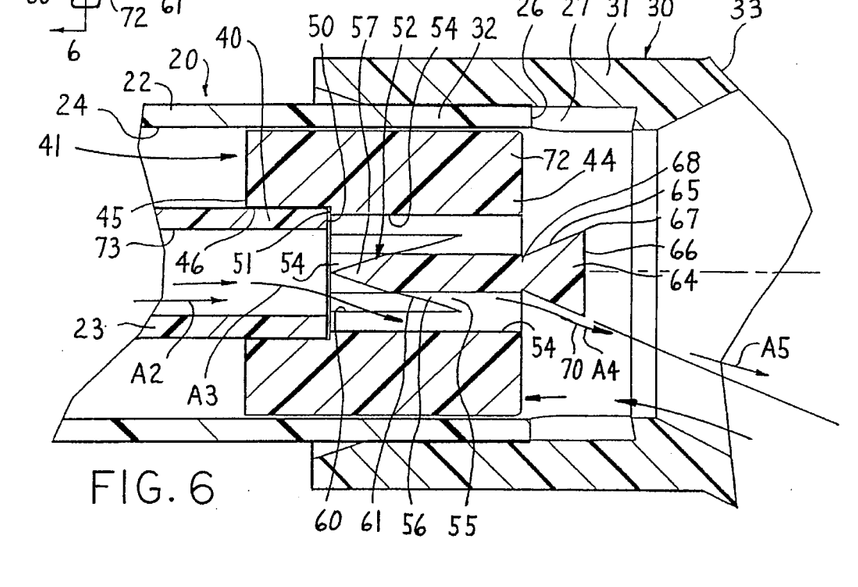
FIG. 6 is a fragmentary, enlarged central cross-sectional view substantially taken on the line 6—6 of FIG. 5.

An array of plural, evenly circumferentially spaced passages 54 extends substantially axially through the body 42 of the tip member 41, from the end wall 51 of the recess 46 forwardly through the distal end wall 44, to open forwardly through the latter. The array of passages 54 coaxially surrounds the conical core 52. The passages 54 define radially outwardly opening grooves 55 in a distal portion 56 of the conical core 52 (FIGS. 5 and 6). The conical core 52 has a proximal end portion 57 which is spaced radially inboard from, and hence is ungrooved by, the axially extending passages 54.

Thus, the portion of the recess extension 46E left open around the conical core 53 (ignoring the passages 54) thus may be termed a space complimentary to the conical core 52. Described in other words, the portion of the tip member body 42 axially between the rear opening recess 46 and the distal end wall 44 is occupied by the conical core 52, the surrounding recess extension 46E, and the proximal portions of the plural passages 54.

Figure 7:
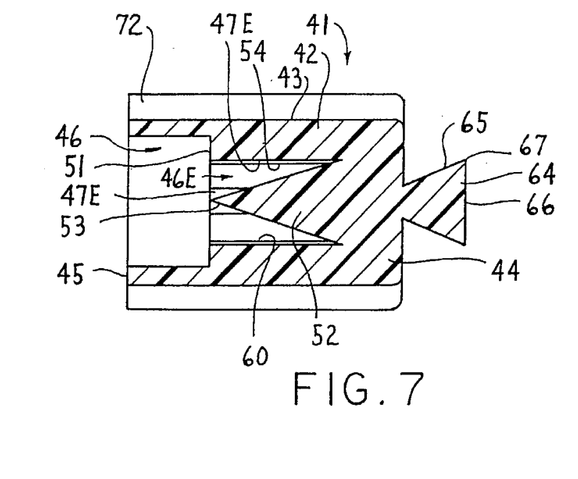
FIG. 7 is a central cross-sectional view of the tip member taken on the line 7—7 of FIG. 5.
Figure 8:
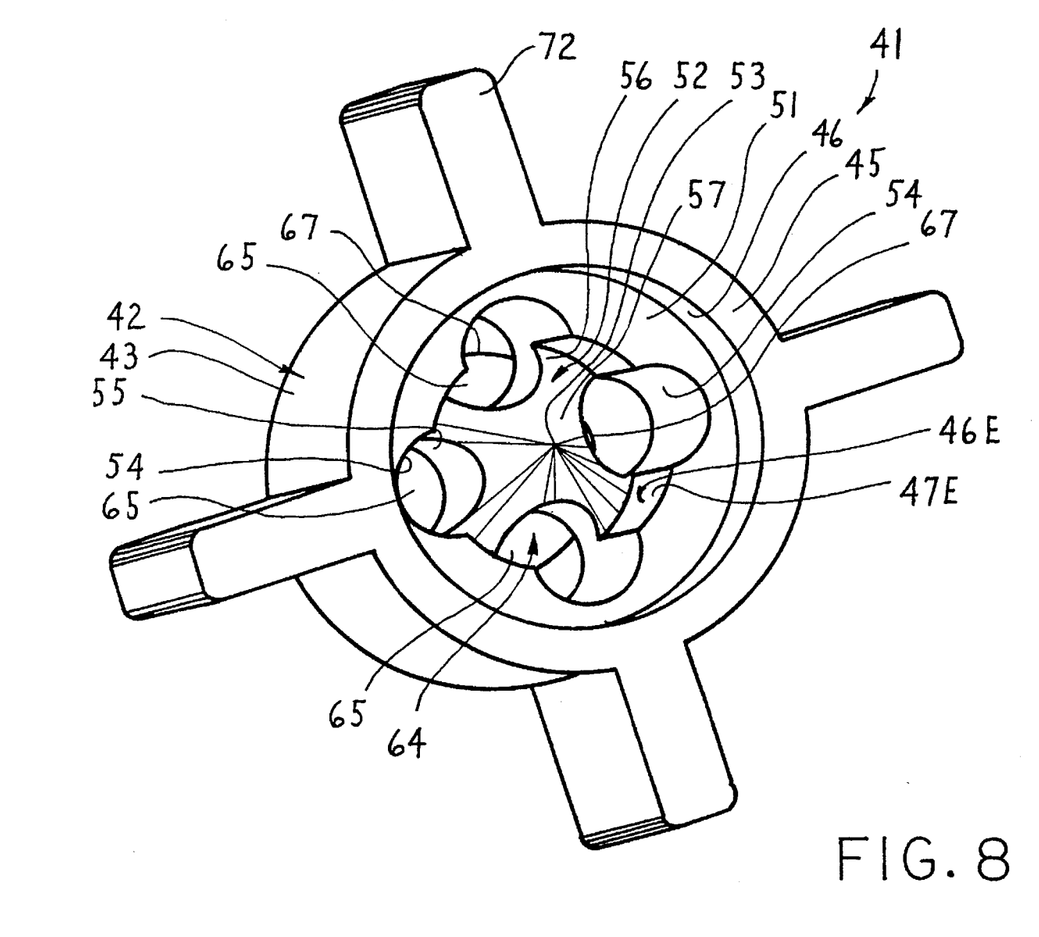
FIG. 8 is an enlarged pictorial view of the FIG. 1 tip member taken generally from the rear end thereof.

In FIGS. 5 and 7, reference numeral 60 indicates the line of intersection between perimeter wall 47E of the recess extension 46E and ones of the passages 54. In FIGS. 5 and 6, reference numeral 61 indicates the line of intersection of the conical core 52 and one of the passages 54.

Figure 4:
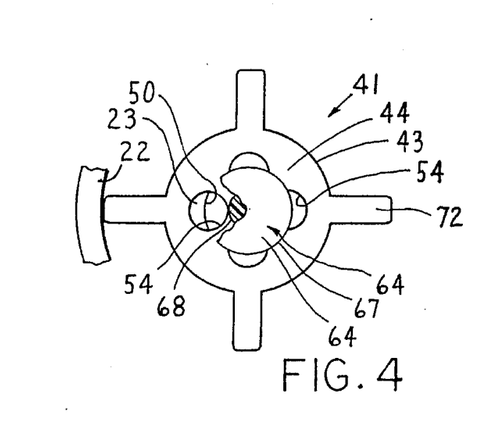
FIG. 4 is an enlarged, partially broken, front view of the FIG. 3 tip member.

A forwardly diverging, substantially conical diverter 64 (FIGS. 3–7) is fixedly and coaxially cantilevered forwardly from the distal wall 44. The diverter 64 has a frustoconical peripheral wall 65 (FIG. 7) and a flat, radially extending forward end wall 66 which meets the frusto-conical peripheral wall 65 at a preferably sharp perimeter edge 67. The rear end 68 of the substantially conical diverter 64 is of diameter to fit snugly between the forward ends of the passages 54 but not overlap same radially, as seen in FIGS. 4 and 6.

The included angles described by (1) the conical core 52, (2) the frustoconical diverter 64, (3) an imaginary conical shell running from the rear tip of the conical core 57 forward past the lip 35 of the spray shield 30 and (4) the inside wall of the frustoconical bell 33 of the spray shield 30 progressively increase. In the embodiment shown, such included angles are about (1) 36°, (2) 47°, (3) 50° and (4) 56° respectively.

The conical core 52 and frustoconical diverter 64 thus progressively diverge the irrigation liquid flow as it flows forwardly therepast. The sharpness of the perimeter edge 67 at the forward end of the diverter 64 minimizes the tendency of the forward irrigation flow to bend radially inward and become turbulent in front of the diverter 64, and instead helps the flow separate cleanly from the diverter forward end wall 66, as indicated at 70 on the arrow A4 in FIG. 6. The irrigation flow continuing forward out through the spray shield 30 has, as indicated by the arrow A5, a somewhat lesser angle of divergence than the spray shield itself so that the flow does not tend to significantly impact, or adhere to, the interior surface of the bell 33 and lip 35 of the spray shield 30. The irrigation liquid flows forward from the tip member 41 and thus defines a hollow frustoconical shell of forward moving liquid.

Plural, preferably four, evenly circumferentially spaced fins 72 (FIGS. 3–7) extend along and radially out from the outer perimeter surface 43 of the body 42. As seen in FIG. 3, the fins 72 are each substantially rectangular in a longitudinal/radial plane. The fins 72 are substantially equal in radial extent to center the body 42 and irrigation tube 23 in the suction tube 22. The fins 72 (FIGS. 4 and 6) here extend substantially the length of the body 42 and contact the suction tube 22 to steady the body 42 and irrigation tube 23 within the suction tube 22.

OPERATION

The tip member 41 is preferably molded in one piece. It is thus convenient for the body 42 to carry four evenly circumferentially spaced (at 90° circumferential separation) fins 72.

The tip member 41 can be fixed to the distal end of the irrigation tube 23 prior to insertion of the irrigation tube 23 into the suction tube 22, during assembly of the wand 20. The fins 72 are an axially sliding fit within the suction tube 22. The wand 20 may be permanently affixed to the handpiece barrel 12, but is preferably releasably connected thereto by the known (e.g. EXCEL (TM) or SURGILAV PLUS (TM)) releasable connection schematically indicated at 21, to allow use alternatively of different wands, for example provided with different tip members 41, with the same handpiece 10. Similarly, a given wand 20 can be used with or without the removable spray shield. Indeed, during surgery, different wands 20 can be interchanged preferably on the same handpiece 10 and a spray shield 30 can be placed on or removed from the wand 20 to be used.

In operation, the handpiece 10 is conventionally connected to the irrigation liquid source IL, electric power source EP and suction source SS, as schematically indicated in FIG. 1. Actuation of the switch SW, by hand actuation of the trigger T, energizes the motor M from the electrical power source EP, to activate the pulsing pump P, which draws irrigation liquid from the irrigation liquid source IL and outputs a series of irrigation liquid pulses through the irrigation tube 23 and tip member 41, toward the area of the surgical site surface SU to be cleaned.

At the same time, flowable material, such as expelled irrigation liquid and bits of patient tissue entrained therein, is drawn into the distal end of the suction tube 22 past the fins 72 of, and along the outer perimeter surface 43 of, the tip member 41, thence rearward along the annular suction passage 24 (FIG. 1) between the suction and irrigation tubes 22 and 23, and thence along the suction path schematically indicated at 25 in the handpiece, to the suction source SS. The fins 72, the tip member outer perimeter surface 43 and the interior surface of the suction tube 22 act together, as a sort of four hole screen, to limit the size of solid particles to be drawn into the annular suction passage 24.

It will be noted that the tip member 41 is somewhat axially recessed within the suction tube 22 so that the forwardmost portion of the tip member, namely the diverter 64, is spaced slightly rearward from the front end of the suction tube 22. Thus, even with the spray shield 30 removed from the suction tube 22, the distal end of the suction tube can be brought into contact with a given surface, such as the surgical site surface SU, without physical contact of the surface SU with the tip member 41. At the same time, however, the tip member 41 is close enough to the front end of the suction tube 22 that irrigation liquid flow forward out of the passages 54 and beyond the diverter 64 can diverge, as caused by the tip member 41, without significant constraint by the front end of the suction tube 22 (and indeed without significant constraint by the spray shield 30 when the latter is in place on the front end of the suction tube).

Attention is now specifically directed to the pattern of irrigation flow. The particular handpiece 10, here shown for purposes of illustration of environment, forwards irrigation liquid to the irrigation tube 23 in a series of pulses. The above-mentioned SURGILAV PLUS (TM) device is for example capable of about 1200 irrigation liquid pulses per minute outputted past the tip member 41, with a force of about 0.4 to 0.6 Newtons, and a flow rate of about 1200 to 1400 milliliters per minute, although substantial variations up and down from those numbers are contemplated. In any event, irrigation liquid flow forward from the pump P is schematically indicated by the arrows A1, A2, A3, A4, A5 in FIGS. 1 and 6.

It will be noted that the interior bore 73 (FIG. 6) of the irrigation tube 23 is less than that of an imaginary circle closely bounding the passages 54. Indeed, the inside diameter (indicated at 73 of FIG. 6) of the irrigation tube 23 is about the same as the outside diameter of the forward end wall 66 of the diverter 64, as also seen in FIG. 4. Thus, as irrigation liquid flows forward (see arrow A3 in FIG. 6) through the tip member 41, it is angled outward by the proximal end 57 of the conical core 52 and by location of the radially outer parts of the passages 54 radially outboard of the irrigation tube 23. Irrigation liquid then passes forwardly out of the passages 54 and is further diverted radially outwardly by the frustoconical peripheral wall 65 of the diverter 64. The sharp perimeter 67 and radially flat, forward end wall 66 of the diverter 64 provides for clean flow separation from the diverter 64 as irrigation liquid flow continues forwardly therebeyond, allowing only a few degrees of convergence of the irrigation flow as indicated by the portion 70 of the arrow A4. The result is a divergent, generally funnel-shaped irrigation liquid flow forward from a distal end of the suction tube 22, as generally indicated by the arrow A5 in FIG. 6, at an included angle slightly less than required to clear the lip 35 of the spray shield 30, in case the apparatus is being used with such a spray shield. The pulsed flow of irrigation liquid forward from the wand 20 is very schematically indicated by the generally frustoconical shaped rings R5, R6, and R7 in FIG. 2. The irrigation liquid does tend to be forwardly projected from the tip member 41 as a series of discrete, increasing diameter rings, though of course with cross-sectional shape less sharply defined than schematically shown in FIG. 2. The irrigation liquid projected forwardly from the tip member 41 does form circumferentially continuous rings. A given liquid pulse, projected forwardly from the circumferentially spaced forward ends of the passages 54, spreads circumferentially, to form a ring, due, for example, to circumferential turbulence in the irrigation liquid pulse as it is circumferentially channeled from the distal end 50 of the irrigation tube 23 into the four passages 54, to edge effects at the front ends of the passages 54, and to surface effects in contacting the frustoconical peripheral wall and sharp front perimeter edge 67 of the conical diverter 64. In any event, the irrigation liquid pulses projected forwardly and divergently from the front end of the tip member 41 have a ring-like character, rather than appearing as four circumferentially separate pulse streams.

The result of the cone-like divergence and resulting circumferential spreading of the irrigation liquid pulses (as schematically indicated at R5, R6 and R7 in FIG. 2) is both to widen the area of impact of a given irrigation liquid pulse with the surgical site surface SU and also to somewhat reduce the force of impact therewith, so as to facilitate cleaning foreign matter and damaged tissue from a large area trauma site and minimize possible injury to exposed healthy tissue at the surface of the trauma site. The latter enables use on delicate tissue, cleanup operations, of a strong irrigation liquid pulse producing handpiece (such as the SURGILAV PLUS (TM) handpiece above-mentioned), which is intended for more difficult tissue debris separation in more durable surgical site surfaces (such as cleaning out the interior of a femoral cavity preparatory to cementing in of a hip joint stem).

Passages 54 are intentionally of large diameter, to restrict irrigation flow forwardly therethrough as little as possible. As seen for example in FIG. 5, the minimum circumferential spacing between adjacent passages 54 is less than half the diameter of the passages 54. Further, as seen in FIG. 5, the passages 54 are located to extend radially outward well beyond the inner surface of the bore 73 of the irrigation tube 23. Both these features increase the total flow cross section of four passages 54 relative to the diameter of the bore 73 of the irrigation tube 23, so as to minimize flow restriction by the passages 54. Separation of the flow into the flow passages 54 is needed to provide a rigid support for the conical core 52 and diverter 64 centrally of the tip member 41. Thus, although the conical core 52 and diverter 64 are both rigidly supported with respect to the irrigation tube 23, the flow cross section area through the tip member 41 is almost as large (for example about 85%) as the flow cross section within the irrigation tube 23.

Thus, the tip member 41 effectively reduces irrigation liquid pulse impact force and resulting potential damage to delicate trauma site tissues while spreading the area of irrigation liquid contact at the site SU, but without substantially reducing the rate of irrigation liquid volume delivery to the site, all with a handpiece 10 normally producing higher impact pulses than normally appropriate for delicate trauma site cleaning.

Although a particular preferred embodiment of the invention has been disclosed in detail for illustrative purposes, it will be recognized that variations or modifications of the disclosed apparatus, including the rearrangement of parts, lie within the scope of the present invention.

The embodiments of the invention in which an exclusive property or privilege is claimed are defined as follows:

1. A surgical irrigation wand for a surgical irrigation handpiece, comprising:

means defining a surgical irrigation tube for connection to an irrigation liquid outlet of a surgical irrigation handpiece, said tube having a distal end for directing irrigation liquid flow forwardly toward a surgical site;

tip means for shaping said flow into a hollow, divergent, substantially circumferentially continuous, generally funnel-shaped wash of irrigation liquid and thereby for wetting substantially the perimeter of a circle, rather than the center of such circle, on the surgical site at a given instant, said tip means comprising a proximal end fixed adjacent said distal end of said tube, a distal end defined by a distal end wall, and a forward diverging, substantially conical diverter fixedly and coaxially extending forward from said distal end wall of said body for diverging the flow of irrigation liquid forwardly beyond said tip means toward said surgical site.

2. The apparatus of claim 1 wherein said tip means comprises an elongate body having:

an outer perimeter surface;

said distal end wall;

said proximal end having a central, coaxial, proximally opening recess for receiving said irrigation tube distal end;

a central, coaxial core having a substantially conical perimeter surface tapering rearward from said distal end wall for forwardly diverging the flow of irrigation liquid therealong, said core being rearwardly fixedly cantilevered from said distal end wall and disposed coaxially with said proximally opening recess;

an array of plural, circumferentially spaced passages extending generally axially through said distal end wall for channeling the diverged flow of irrigation liquid forwardly through said distal end wall, said array coaxially surrounding said conical core, said passages defining grooves in a distal portion of the substantially conical perimeter surface of said core, said conical core having a proximal end portion ungrooved by said passages.

3. The apparatus of claim 2 in which said proximal recess is sized to snugly receive therein the distal end of said irrigation tube, said tip means being cantilevered forwardly from said irrigation tube.

4. The apparatus of claim 2 including surface means in said body and formed by said conical core, conical diverter and passages for diverging the flow of irrigation liquid forwardly beyond said tip means toward a surgical site.

5. The apparatus of claim 1 in which said proximal end of said tip means includes a central, coaxial, proximally opening recess which is sized to snugly receive therein a distal end of an irrigation tube, the tip means being cantilevered forwardly from said irrigation tube.

6. The apparatus in claim 5 including plural circumferentially spaced fins extending along and radially out from an outer perimeter surface of said tip means, said fins being substantially rectangular in a longitudinal/radial plane, said fins being substantially equal in radial extent to center said tip means and said irrigation tube in a surrounding suction tube of a surgical irrigation handpiece wand, said fins extending substantially the length of said body and adapted to contact such a suction tube at least at the ends of said fins for steadying said body and such an irrigation tube in such a suction tube.

7. The apparatus of claim 1, wherein said conical diverter is defined by a frustoconical peripheral wall and a forward end wall which meets said peripheral wall at a sharp perimeter edge to facilitate separation of the irrigation liquid flow from said diverter.

8. A surgical irrigation wand for a surgical irrigation handpiece, comprising:

means defining a surgical irrigation tube for connection to an irrigation liquid outlet of a surgical irrigation handpiece, said tube having a distal end for directing irrigation liquid flow forwardly toward a surgical site;

means defining a suction tube for connection to a suction port of said surgical irrigation handpiece, said suction tube substantially coaxially surrounding said irrigation tube;

tip means fixed adjacent said distal end of said tube for shaping said flow into a hollow, divergent, substantially circumferentially continuous, generally funnel-shaped wash of irrigation liquid and thereby for wetting substantially the perimeter of a circle, rather than the center of such circle, on the surgical site at a given instant, said tip means comprising an elongate body having:

an outer perimeter surface;
a distal end wall;
a proximal end having a central, coaxial, proximally opening recess for receiving said irrigation tube distal end;
surface means for diverging the irrigation flow forwardly beyond said tip means toward a surgical site comprising:
a central, coaxial core having a substantially conical perimeter surface tapering rearward from said distal end wall for forwardly diverging the flow of irrigation liquid therealong, said core being rearwardly fixedly cantilevered from said distal end wall and disposed coaxially with said proximally opening recess;
an array of plural, circumferentially spaced passages extending generally axially through said distal end wall for channeling the diverged flow of irrigation liquid forwardly through said distal end wall, said passages defining grooves in a distal portion of the substantially conical perimeter surface of said core; and plural circumferentially spaced fins extending along and radially out from said outer perimeter surface of said body, said fins being substantially rectangular in a longitudinal/radial plane, said fins being substantially equal in radial extent to center said body and irrigation tube in said suction tube, said fins extending substantially the length of said body and contacting said suction tube at least at the ends of said fins for steadying said body and irrigation tube in said suction tube.

9. A surgical irrigation wand for a surgical irrigation handpiece, comprising:

means defining a surgical irrigation tube for connection to an irrigation liquid outlet of a surgical irrigation handpiece, said tube having a distal end for directing irrigation liquid flow forwardly toward a surgical site;

tip means fixed adjacent said distal end of said tube for shaping said flow into a hollow, divergent, substantially circumferentially continuous, generally funnel-shaped wash of irrigation liquid and thereby for wetting substantially the perimeter of a circle, rather than the center of such circle, on the surgical site at a given instant, said tip means comprising an elongate body having:

an outer perimeter surface;
a distal end wall;
a proximal end having a central, coaxial, proximally opening recess for receiving said irrigation tube distal end;
surface means for diverging the flow of irrigation liquid forwardly beyond said tip means toward a surgical site comprising:
a central, coaxial core having a substantially conical perimeter surface tapering rearward from said distal end wall for forwardly diverging the flow of irrigation liquid therealong, said core being rearwardly fixedly cantilevered from said distal end wall and disposed coaxially with said proximally opening recess;
an array of plural, circumferentially spaced passages extending generally axially through said distal end wall for channeling the diverged flow of irrigation liquid forwardly through said distal end wall, said passages defining grooves in a distal portion of the substantially conical perimeter surface of said core; and
a substantially funnel-shaped spray shield extending forwardly beyond said irrigation tube and having a proximal collar portion sleeved on said distal end of said irrigation tube and having a wide distal mouth placeable close to a surface of a surgical site to limit sideward splashing of liquid from the surgical site during irrigation thereof, the included angle of said spray shield exceeding the included angle of divergence of irrigation flow forward from said tip unit to avoid interference of the spray shield with irrigation liquid flow from said tip unit to a surgical site.

10. A surgical irrigation wand for a surgical irrigation handpiece, comprising:

means defining a surgical irrigation tube for connection to an irrigation liquid outlet of a surgical irrigation handpiece, said tube having a distal end for directing irrigation liquid flow forwardly toward a surgical site;

tip means fixed adjacent said distal end of said tube for shaping said flow into a hollow, divergent, substantially circumferentially continuous, generally funnel-shaped wash of irrigation liquid and thereby for wetting substantially the perimeter of a circle, rather than the center of such circle, on the surgical site at a given instant, said tip means comprising an elongate body having:

an outer perimeter surface;

a distal end wall;

a proximal end having a central, coaxial, proximally opening recess for receiving said irrigation tube distal end; and surface means for diverging the flow of irrigation liquid forwardly beyond said tip means toward a surgical site comprising:

a central, coaxial core having a substantially conical perimeter surface tapering rearward from said distal end wall for forwardly diverging the flow of irrigation liquid therealong, said core being rearwardly fixedly cantilevered from said distal end wall and disposed coaxially with said proximal opening recess;

an array of plural, circumferentially spaced passages extending generally axially through said distal end wall for channeling the diverged flow of irrigation liquid forwardly through said distal end wall, said passages defining grooves in a distal portion of the substantially conical perimeter surface of said core; and a forward diverging, substantially conical diverter fixedly and coaxially extending forward from said distal end wall of said body.

11. A surgical irrigation handpiece unit, comprising:

a handpiece including means for forwardly projecting irrigation liquid forcibly toward a site on a patient to be treated;

means defining a wand including an irrigation liquid tube projecting forwardly from said handpiece toward a site on a patient;

means defining a suction tube for connection to a suction port of a surgical irrigation handpiece, said suction tube substantially coaxially surrounding said irrigation tube;

tip means fixed adjacent a distal end of said tube and cantilevered forwardly from said tube for shaping irrigation liquid flow through the tube into a hollow, divergent, substantially circumferentially continuous, generally funnel-shaped wash of irrigation liquid and thereby for wetting substantially the perimeter of a circle, rather than the center of such circle, on a site on a patient to be treated, said tip means comprising an elongate body having:

an outer perimeter surface;

a distal end wall;

a proximal end having a central, coaxial, proximally opening recess for receiving said irrigation tube distal end;

surface means for diverging the flow of irrigation liquid forwardly beyond said tip means toward a surgical site comprising:

a central, coaxial core having a substantially conical perimeter surface tapering rearward from said distal end wall for forwardly diverging the flow of irrigation liquid therealong, said core being rearwardly fixedly cantilevered from said distal end wall and disposed coaxially with said proximally opening recess;

an array of plural, circumferentially spaced passages extending generally axially through said distal end wall for channeling the diverged flow of irrigation liquid forwardly through said distal end wall, said passages defining grooves in a distal portion of the substantially conical perimeter surface of said core; and plural circumferentially spaced fins extending along and radially out from said outer perimeter surface of said body, said fins being substantially rectangular in a longitudinal/radial plane, said fins being substantially equal in radial extent to center said body and irrigation tube in said suction tube, said fins extending substantially the length of said body and contacting said suction tube at least at the ends of said fins for steadying said body and irrigation tube in said suction tube.

12. A surgical irrigation handpiece unit, comprising:

a handpiece including means for forwardly projecting irrigation liquid forcibly toward a site on a patient to be treated;

means defining a wand including an irrigation liquid tube projecting forwardly from said handpiece toward a site on a patient;

tip means fixed adjacent a distal end of said tube for shaping irrigation liquid flow through the tube into a hollow, divergent, substantially circumferentially continuous, generally funnel-shaped wash of irrigation liquid and thereby for wetting substantially the perimeter of a circle, rather than the center of such circle, on a site on a patient to be treated, said tip means comprising an elongate body having:

an outer perimeter surface;

a distal end wall;

a proximal end having a central, coaxial, proximally opening recess for receiving said irrigation tube distal end;

surface means for diverging the flow of irrigation liquid forwardly beyond said tip means toward a surgical site comprising:

a central, coaxial core having a substantially conical perimeter surface tapering rearward from said distal end wall for forwardly diverging the flow of irrigation liquid therealong, said core being rearwardly fixedly cantilevered from said distal end wall and disposed coaxially with said proximally opening recess;

an array of plural, circumferentially spaced passages extending generally axially through said distal end wall for channeling the diverged flow of irrigation liquid forwardly through said distal end wall, said passages defining grooves in a distal portion of the substantially conical perimeter surface of said core; and a substantially funnel-shaped spray shield extending forwardly beyond said irrigation tube and having a proximal collar portion sleeved on said distal end of said irrigation tube and having a wide distal mouth placeable close to a surface of a surgical site to limit sideward splashing of liquid from the surgical site during irrigation thereof, the included angle of said spray shield exceeding the included angle of divergence of irrigation flow forward from said tip unit to avoid interference of the spray shield with irrigation liquid flow from said tip unit to a surgical site.

13. A surgical irrigation wand for a surgical irrigation handpiece, comprising:

means defining a surgical irrigation tube for connection to an irrigation liquid outlet of a surgical irrigation handpiece, said tube having a distal end for directing irrigation liquid flow forwardly toward a surgical site;

means defining a suction tube for connection to a suction port of a surgical irrigation handpiece, said suction tube substantially coaxially surrounding said irrigation tube;

tip means for shaping said flow into a hollow, divergent, substantially circumferentially continuous, generally funnel-shaped wash of irrigation liquid and thereby for wetting substantially the perimeter of a circle, rather than the center of such circle, on the surgical site at a given instant, said tip means comprising a proximal end fixed adjacent said distal end of said irrigation tube, a distal end and a plurality of circumferentially spaced fins extending along and radially out from an outer perimeter surface of said tip means, said fins being substantially equal in radial extent to center said tip means and irrigation tube in said suction tube, said fins contacting said suction tube at least at the ends of said fins for steadying said tip means and irrigation tube in said suction tube.

14. The apparatus of claim 13 in which said tip means comprises an elongate body having:

said outer perimeter surface;

a distal end wall;

said proximal end having a central, coaxial, proximally opening recess for receiving said irrigation tube distal end; and surface means for diverging the flow of irrigation liquid forwardly beyond said tip means toward said surgical site comprising:

a central, coaxial core having a substantially conical perimeter surface tapering rearward from said distal end wall for forwardly diverging the flow of irrigation liquid therealong, said core being rearwardly fixedly cantilevered from said distal end wall and disposed coaxially with said proximally opening recess; and an array of plural, circumferentially spaced passages extending generally axially through said distal end wall for channeling the diverged flow of irrigation liquid forwardly through said distal end wall, said array coaxially surrounding said conical core, said passages defining grooves in a distal portion of the substantially conical perimeter surface of said core, said conical core having a proximal end portion ungrooved by said passages.

15. The apparatus of claim 14 in which said proximal recess is sized to snugly receive therein the distal end of said irrigation tube, said tip means being cantilevered forwardly from said irrigation tube.

16. The apparatus of claim 13 including surface means in said tip means and formed by a conical core and passages therethrough for diverging the flow of irrigation liquid forwardly beyond the distal end toward a surgical site.

17. The apparatus of claim 16 in which said surface means includes surfaces of said conical core and passages and further includes a forward diverging, substantially conical diverter fixedly and coaxially extending forward from distal end wall of said tip means.

* * * * *

UNITED STATES PATENT AND TRADEMARK OFFICE
CERTIFICATE OF CORRECTION

PATENT NO. : 5,460,604
DATED : October 24, 1995
INVENTOR(S) : Jeffrey D. ARNETT, et al.

It is certified that error appears in the above-indentified patent and that said Letters Patent is hereby corrected as shown below:

Column 14, line 31; after "from" insert ---a---.

Signed and Sealed this

Twentieth Day of February, 1996

Attest:

BRUCE LEHMAN

Attesting Officer
Commissioner of Patents and Trademarks